United States Patent
Styczynski et al.

(12)

(10) Patent No.: US 6,743,822 B2
(45) Date of Patent: Jun. 1, 2004

(54) REDUCTION OF HAIR GROWTH

(75) Inventors: Peter Styczynski, Wrentham, MA (US); Gurpreet S. Ahluwalia, Potomac, MD (US); Douglas Shander, Acton, MA (US)

(73) Assignee: The Gillette Company, Boston, MA (US)

( * ) Notice: Subject to any disclaimer, the term of this patent is extended or adjusted under 35 U.S.C. 154(b) by 0 days.

(21) Appl. No.: 10/198,219

(22) Filed: Jul. 17, 2002

(65) Prior Publication Data

US 2003/0096871 A1 May 22, 2003

Related U.S. Application Data

(60) Provisional application No. 60/311,651, filed on Aug. 10, 2001.

(51) Int. Cl.$^7$ ............................................. A61K 31/195
(52) U.S. Cl. ........................................................ 514/564
(58) Field of Search ......................................... 514/564

(56) References Cited

U.S. PATENT DOCUMENTS

| | | | |
|---|---|---|---|
| 3,426,137 A | 2/1969 | Philpitt et al. |
| 4,039,669 A | 8/1977 | Beyler et al. |
| 4,139,638 A | 2/1979 | Neri et al. |
| 4,161,540 A | 7/1979 | Neri et al. |
| 4,191,775 A | 3/1980 | Glen |
| 4,269,831 A | 5/1981 | Ferrari et al. |
| 4,370,315 A | 1/1983 | Greff et al. |
| 4,439,432 A | 3/1984 | Peat |
| 4,508,714 A | 4/1985 | Cecic et al. |
| 4,517,175 A | 5/1985 | Iwabuchi et al. |
| 4,720,489 A | 1/1988 | Shander |
| 4,885,289 A | 12/1989 | Breuer et al. |
| 4,935,231 A | 6/1990 | Pigiet |
| 5,095,007 A | 3/1992 | Ahluwalia |
| 5,096,911 A | 3/1992 | Ahluwalia et al. |
| 5,132,293 A | 7/1992 | Shander et al. |
| 5,143,925 A | 9/1992 | Shander et al. |
| 5,189,212 A | 2/1993 | Ruenitz |
| 5,271,942 A | 12/1993 | Heverhagen |
| 5,300,284 A | 4/1994 | Wiechers et al. |
| 5,328,686 A | 7/1994 | Shander et al. |
| 5,362,748 A | 11/1994 | Schwen et al. |
| 5,364,885 A | 11/1994 | Ahluwalia et al. |
| 5,411,991 A | 5/1995 | Shander et al. |
| 5,444,090 A | 8/1995 | Ahluwalia |
| 5,455,234 A | 10/1995 | Ahluwalia et al. |
| 5,468,476 A | 11/1995 | Ahluwalia et al. |
| 5,474,763 A | 12/1995 | Shander et al. |
| 5,554,608 A | 9/1996 | Ahluwalia et al. |
| 5,645,825 A | 7/1997 | Hillebrand et al. |
| 5,648,394 A | 7/1997 | Boxall et al. |
| 5,652,273 A | 7/1997 | Henry et al. |
| 5,674,477 A | 10/1997 | Ahluwalia |
| 5,728,736 A | 3/1998 | Shander et al. |
| 5,776,442 A | 7/1998 | Ahluwalia |
| 5,824,665 A | 10/1998 | Henry et al. |
| 5,840,752 A | 11/1998 | Henry et al. |
| 5,908,867 A | 6/1999 | Henry et al. |
| 5,939,458 A | 8/1999 | Henry et al. |
| 5,958,946 A | 9/1999 | Styczynski et al. |
| 5,962,466 A | 10/1999 | Styczynski et al. |
| 6,020,006 A | 2/2000 | Styczynski et al. |
| 6,037,326 A | 3/2000 | Styczynski et al. |
| 6,060,471 A | 5/2000 | Styczynski et al. |
| 6,093,748 A | 7/2000 | Ahluwalia et al. |
| 6,121,269 A | 9/2000 | Henry et al. |
| 6,218,435 B1 | 4/2001 | Henry et al. |
| 6,235,737 B1 | 5/2001 | Styczynski et al. |
| 6,239,170 B1 | 5/2001 | Ahluwalia et al. |
| 6,248,751 B1 | 6/2001 | Ahluwalia et al. |
| 6,299,865 B1 | 10/2001 | Styczynski et al. |
| 2003/0053973 A1 | 3/2003 | Chou et al. |

FOREIGN PATENT DOCUMENTS

| | | |
|---|---|---|
| EP | 0 413 528 B1 | 8/1990 |
| EP | 0 532 219 A2 | 9/1992 |
| GB | 1 458 349 | 12/1976 |
| WO | 98/02134 | 1/1998 |

OTHER PUBLICATIONS

Botchkarev et al., "A New Role for Neurotrophin–3", *American Journal of Pathology*, vol. 153, pp. 785–799, 1998.

Botchkarev et al., "Neurotrophin–3 Involvement in the Regulation of Hair Follicle Morphogenesis", *The Journal of Investigative Dermatology*, vol. 111, No. 2, pp. 279–285, 1998.

Hoffmann et al., "Interleukin–1 β–Induced Inhibition of Hair Growth In Vitro Is Mediated by Cyclic AMP", *The Journal of Investigative Dermatology*, vol. 108, pp. 40–42, 1997.

Messenger, Andrew G., "The Control of Hair Growth: An Overview", *The Journal of Investigative Dermatology*, vol. 101, No. 1, pp. 4s–9s, 1993.

Weinberg et al., "Reconstitution of Hair Follicle Development In Vitro: Determination of Follicle Formation, Hair Growth, and Hair Quality by Dermal Cells", *The Journal of Investigative Dermatology*, vol. 100, pp. 229–236, 1993.

Ebling, F. John G., "The Biology of Hair", *Dermatologic Clinics*, vol. 5, No. 3, pp. 467–481, 1987.

Hattori et al., "Biochemical Analysis of Hair Growth From the Aspects of Aging and Enzyme Activities", *The Journal of Dermatology*, vol. 10, pp. 45–54, 1983.

Sato, Yoshio, "The Hair Cycle and Its Control Mechanism", pp. 3–13.

Adachi et al., "Human Hair Follicles: Metabolism and Control Mechanisms", *Journal of the Society of Cosmetic Chemists*, vol. 21, No. 13, pp. 901–924, 1970.

*Primary Examiner*—Rebecca Cook
(74) *Attorney, Agent, or Firm*—Fish & Richardson P.C.

(57) ABSTRACT

Hair growth can be reduced using a composition including optically pure L-α-difluoromethylornithine or α-difluoromethylornithine including a preponderance of L-α-difluoromethylornithine.

28 Claims, No Drawings

REDUCTION OF HAIR GROWTH

This application claims the benefit of prior U.S. provisional application 60/311,651, filed Aug. 10, 2001.

BACKGROUND

The invention relates to reducing hair growth in mammals, particularly for cosmetic purposes.

A main function of mammalian hair is to provide environmental protection. However, that function has largely been lost in humans, in whom hair is kept or removed from various parts of the body essentially for cosmetic reasons. For example, it is generally preferred to have hair on the scalp but not on the face.

Various procedures have been employed to remove unwanted hair, including shaving, electrolysis, depilatory creams or lotions, waxing, plucking, and therapeutic antiandrogens. These conventional procedures generally have drawbacks associated with them. Shaving, for instance, can cause nicks and cuts, and can leave a perception of an increase in the rate of hair regrowth. Shaving also can leave an undesirable stubble. Electrolysis, on the other hand, can keep a treated area free of hair for prolonged periods of time, but can be expensive, painful, and sometimes leaves scarring. Depilatory creams, though very effective, typically are not recommended for frequent use due to their high irritancy potential. Waxing and plucking can cause pain, discomfort, and poor removal of short hair. Finally, antiandrogens—which have been used to treat female hirsutism—can have unwanted side effects.

It has previously been disclosed that the rate and character of hair growth can be altered by applying to the skin inhibitors of certain enzymes. These inhibitors include inhibitors of 5-alpha reductase, ornithine decarboxylase, S-adenosylmethionine decarboxylase, gamma-glutamyl transpeptidase, and transglutaminase. See, for example, Breuer et al., U.S. Pat. No. 4,885,289; Shander, U.S. Pat. No. 4,720,489; Ahluwalia, U.S. Pat. No. 5,095,007; Ahluwalia et al., U.S. Pat. No. 5,096,911; and Shander et al., U.S. Pat. No. 5,132,293.

α-Difluoromethylornithine (DFMO) is an irreversible inhibitor of ornithine decarboxylase (ODC), a rate-limiting enzyme in the de novo biosynthesis of putrescine, spermidine, and spermine. The role of these polyamines in cellular proliferation is not yet well understood. However, they seem to play a role in the synthesis and/or regulation of DNA, RNA and proteins. High levels of ODC and polyamines are found in cancer and other cell types that have high proliferation rates.

DFMO binds the ODC active site as a substrate. The bound DFMO is then decarboxylated and converted to a reactive intermediate that forms a covalent bond with the enzyme, thus preventing the natural substrate ornithine from binding to the enzyme. Cellular inhibition of ODC by DFMO causes a marked reduction in putrescine and spermidine and a variable reduction in spermine, depending on the length of treatment and the cell type. Generally, in order for DFMO to cause significant antiproliferative effects, the inhibition of polyamine synthesis must be maintained by continuous inhibitory levels of DFMO because the half-life of ODC is about 30 min, one of the shortest of all known enzymes.

A skin preparation containing DFMO (sold under the name Vaniqa® by Bristol Myers Squibb), has recently been approved by the Food and Drug Administration (FDA) for the treatment of unwanted facial hair growth in women. Its topical administration in a cream based vehicle has been shown to reduce the rate of facial hair growth in women. Vaniqa® facial cream includes a racemic mixture of the "D-" and "L-" enantiomers of DFMO (i.e., D, L-DFMO) in the monohydrochloride form at a concentration of 13.9% by weight active (15%, as monohydrochloride monohydrate). The recommended treatment regimen for Vaniqa® is twice daily. The cream base vehicle in Vaniqa® is set out in Example 1 of U.S. Pat. No. 5,648,394, which is incorporated herein by reference.

It generally takes about eight weeks of continuous treatment before the hair growth-inhibiting efficacy of Vaniqa® cream becomes apparent. Vaniqa® cream has been shown to decrease hair growth an average of 47%. In one study, clinical successes were observed in 35% of women treated with Vaniqa® cream. These women exhibited marked improvement or complete clearance of their condition as judged by physicians scoring a decrease in visibility of facial hair and a decrease in skin darkening caused by hair. Another 35% of the women tested experienced some improvement in their condition. However, there were some women who exhibited little or no response to treatment.

Accordingly, although Vaniqa® cream is an effective product, it would be even more effective if it provided an earlier onset of hair growth inhibition (i.e., exhibited efficacy earlier than eight weeks) and/or exhibited an increased clinical success rate (i.e., exhibited efficacy in a greater percentage of users). Such improved results cannot be obtained by simply increasing the concentration of D, L-DFMO in the cream vehicle. First, increasing the concentration of D, L-DFMO above about 14% can cause increased stinging of the skin and/or can leave a residue, making it aesthetically unacceptable. Second, it is difficult to formulate compositions with an active concentration above about 15% because significantly higher concentrations of D,L-DFMO are not adequately soluble in the vehicle or destabilize the emulsion.

Molecules that are identical to each other in chemical structural formula and yet are not superimposable upon each other are enantiomers. In terms of their physiochemical properties enantiomers differ only in their ability to rotate the plane of plane-polarized light, and this property is frequently used in their designation. Those entiomers that rotate plane-polarized light to the right are termed dextrorotatory, indicated by either a (+)- or d- or D- before the name of the compound; those that rotate light to the left are termed laevorotatory indicated by a (−)- or l- or L-prefix. A racemic mixture is indicated by either a (±)- or d,1- or D,L- prefix. By another convention (or nomenclature), the R,S or the sequence rule can be used to differentiate enantiomers based on their absolute configuration. Using this system the L-DFMO corresponds to the R-DFMO, and the D-DFMO corresponds to the S-DFMO. Enantiomers are physiochemically similar in that they have similar melting points, boiling points, relative solubility, and chemical reactivity in an achiral environment. A racemate is a composite of equal molar quantities of two enantiomeric species, often referred to as the DL-form. Individual enantiomers of chiral molecules may possess different pharmacological profiles, i.e., differences in pharmacokinetics, toxicity, efficacy, etc.

SUMMARY

The present invention provides a method (typically a cosmetic method) of reducing unwanted human hair growth by applying to the skin a dermatologically acceptable topical composition comprising α-difluoromethylornithine (DFMO) in an amount effective to reduce hair growth, wherein the α-difluoromethylornithine comprises at least about 70% by weight of L-α-difluoromethylornithine (L-DFMO). The unwanted hair growth may be undesirable from a cosmetic standpoint or may result, for example, from a disease or an abnormal condition (e.g., hirsutism). Preferably the DFMO will comprise at least about 80%, more preferably at least about 90%, most preferably at least about 95% of the L-DFMO. Ideally, the DFMO will be substantially optically pure L-DFMO. "Substantially optically pure" means that the DFMO comprises at least 98% L-DFMO. "Optically pure" L-DFMO means that the DFMO comprises essentially 100% L-DFMO. DFMO, as used herein, includes DFMO itself and pharmaceutically acceptable salts thereof.

The present invention also relates to topical compositions comprising a dermatologically or cosmetically acceptable vehicle and α-difluoromethylornithine (DFMO) in an amount effective to reduce hair growth, wherein the α-difluoromethylornithine comprises at least about 70% by weight of L-α-difluoromethylornithine (L-DFMO). In addition, the present invention relates to the use of α-difluoromethylornithine for the manufacture of a therapeutic topical composition for reducing hair growth, wherein the α-difluoromethylornithine comprises at least about 70% by weight of L-α-difluoromethylornithine (L-DFMO).

The above compositions containing a preponderance of L-DFMO have an enhanced efficacy relative to similar compositions containing racemic D,L-DFMO. This enhanced efficacy can manifest itself, for example, in earlier onset of hair growth inhibiting activity, greater reduction of hair growth rate, and/or greater number of subjects demonstrating reduced hair growth. As a result, a composition using the same vehicle as Vaniqa® cream, but including about 10%–15% by weight of, for example, substantially optically pure L-DFMO, is more effective, in terms of onset of efficacy and rate of clinical success than Vaniqa® cream. Preferred compositions include about 0.1% to about 30%, preferably about 1% to about 20%, more preferably about 5% to about 15%, by weight of the DFMO, as described above, and produce less stinging than Vaniqa® cream.

Some preferred compositions (1) provide an average inhibition of at least 35%, more preferably at least 40%, when tested at a DFMO concentration of 0.3% in the Golden Syrian Hamster assay; (2) exhibit efficacy in at least 60%, more preferably at least 70%, most preferably at least 80% of Golden Syrian Hamsters, when tested at a DFMO concentration of 2% in the Golden Syrian Hamster Assay; (3) exhibit maximal efficacy in at least 40%, more preferably at least 50%, most preferably at least 55% of Golden Syrian Hamsters, of the time when tested at a DFMO concentration of 2% in the Golden Syrian Hamster assay; (4) provide an average inhibition of hair growth of at least 15%, more preferably at least 20%, most preferably at least 25%, when tested at a DFMO concentration of 1% in the twice a week Golden Syrian Hamster assay; (5) provide an average reduction of hair follicle spatial mass of at least 35%, more preferably at least 45%, most preferably at least 50%, when tested at a DFMO concentration of 0.5% in the Golden Syrian Hamster hair follicle mass assay; and/or (6) provide an average reduction of hair follicle density of at least 20%, more preferably at least 30%, most preferably at least 35%, when tested at an DFMO concentration of 0.5% in the Golden Syrian Hamster hair follicle density assay. The DFMO also preferably includes sufficient L-DFMO to provide a hair follicle growth inhibition of at least 15%, more preferably at least 25%, most preferably at least 30%, when tested in the Human Hair Follicle Growth assay at a concentration of 0.5 mM. These assays will be described in detail below. A "DFMO concentration of", when used in connection with these assays means that prior to testing the composition in an assay the amount of DFMO used in the composition has been adjusted to provide the concentration listed for the assay, with corresponding adjustments to the other components of the composition.

Preferred compositions of the present invention provide (1) significantly earlier onset (e.g., less than six weeks, preferably less than four weeks) of reduced facial hair growth than Vaniqa® cream in women when applied twice daily; (2) a substantial reduction (as exhibited by marked improvement or complete clearance) of facial hair in at least 50% of women when applied twice a day or less frequently; (3) a substantially complete clearance of facial hair in at least 25% of women when applied twice a day or less frequently; (4) at least approximately the same efficacy of Vaniqa® cream (when the Vaniqa® cream is applied twice a day) when applied once a day to facial area in women.

Other features and advantages of the invention will be apparent from the description and the claims which follow.

DETAILED DESCRIPTION

The preferred composition includes substantially optically pure L-DFMO or DFMO including a preponderance of L-DFMO in a cosmetically and/or dermatologically acceptable vehicle. The composition may be a solid, semi-solid, or liquid. The composition may be, for example, a cosmetic and dermatologic product in the form of an, for example, ointment, lotion, foam, cream, gel, or solution. The composition may also be in the form of a shaving preparation or an aftershave. The vehicle itself can be inert or it can possess cosmetic, physiological and/or pharmaceutical benefits of its own.

The composition may include one or more other types of hair growth reducing agents, such as those described in U.S. Pat. No. 5,364,885 or U.S. Pat. No. 5,652,273.

The concentration of DFMO in the composition may be varied over a wide range up to a saturated solution, preferably from 0.1% to 30% by weight; the reduction of hair growth increases as the amount of DFMO applied increases per unit area of skin. The maximum amount effectively applied is limited only by the rate at which the DFMO penetrates the skin. The effective amounts may range, for example, from 10 to 3000 micrograms or more per square centimeter of skin.

Vehicles can be formulated with liquid or solid emollients, solvents, thickeners, humectants and/or powders. Emollients include, for example, stearyl alcohol, mink oil, cetyl alcohol, oleyl alcohol, isopropyl laurate, polyethylene glycol, olive oil, petroleum jelly, palmitic acid, oleic acid, and myristyl myristate. Solvents include, for example, water, ethyl alcohol, isopropanol, acetone, diethylene glycol, ethylene glycol, dimethyl sulfoxide, and dimethyl formamide. A preferred vehicle for compositions of the present invention is described in U.S. Pat. No. 5,648,394.

The composition also may include components that enhance the penetration of the compound into the skin and/or to the site of action. Examples of penetration enhancers include urea, polyoxyethylene ethers (e.g., Brij-derivatives), terpenes (e.g., nerolidol or 3-hydroxy-3,7,11-trimethyl-1,6,10-dodecatriene), cis-fatty acids (e.g., oleic acid, palmitoleic acid), acetone, laurocapram, dimethyl sulfoxide, 2-pyrrolidone, oleyl alcohol, glyceryl-3-stearate, propan-2-ol, myristic acid isopropyl ester, and propylene glycol.

The composition also can be formulated to provide a reservoir within or on the surface of the skin to provide for a continual slow release of the DFMO. The composition also may be formulated to evaporate slowly from the skin, allowing the inhibitor extra time to penetrate the skin.

Optically pure L-DFMO and optically pure D-DFMO can be prepared by known methods. See, for example, U.S. Pat. No. 4,309,442, Gao et al., Ann. Pharm. Fr. 52(4):184–203 (1994); Gao et al., Ann. Pharm. Fr. 52(5):248–59 (1994); and Jacques et al., Tetrahedron Letters, 48:4617 (1971), all of which are incorporated by reference herein.

The following are examples of compositions.

EXAMPLE 1

A composition contains up to 15% by weight of substantially optically pure L-DFMO, or DFMO comprising a preponderance of L-DFMO, in a vehicle containing water 68%, ethanol 16%, propylene glycol 5%, dipropylene glycol 5%, benzyl alcohol 4%, and propylene carbonate 2%.

EXAMPLE 2

A composition contains up to 15% by weight of substantially optically pure L-DFMO, or DFMO comprising a preponderance of L-DFMO, in a vehicle containing water 80.84%, glyceryl stearate 4.24%, polyethylene glycol 100-stearate 4.09%, cetearyl alcohol 3.05%, ceteareth-20 2.5%, mineral oil 2.22%, stearyl alcohol 1.67%, dimethicone 0.56%, and a preservative.

EXAMPLE 3

Any one or more of the previous examples in combination with one or more of the penetration enhancers selected from: urea, polyoxyethylene-4-lauryl ether (Brij-30; Laureth-4), 3-hydroxy-3,7,11-trimethyl-1,6,10-dodecatriene (nerolidol), and/or cis-9-octadecanoic acid (oleic acid).

EXAMPLE 4

Examples 1–3 with penetration enhancers including, but not restricted to, the following list: propan-2-ol, polyoxyethylene ethers, terpenes, cis-fatty acids (oleic acid, palmitoleic acid), acetone, laurocapram, dimethyl sulfoxide, 2-pyrrolidone, oleyl alcohol, glyceryl-3-stearate, cholesterol, myristic acid isopropyl ester, and propylene glycol. A penetration enhancer may be added at a concentration of, for example, 0.10% to 20% by weight. The preferred concentration is 0.5% to 10% by weight.

EXAMPLE 5

A composition contains 15% by weight substantially optically pure L-DFMO in a vehicle containing water 72.76%, glyceryl stearate 3.82%, polyethylene glycol 100-stearate 3.68%, cetearyl alcohol 2.74%, ceteareth-20 7.25%, urea 5%, mineral oil 2%, stearyl alcohol 1.5%, dimethicone 0.51%, and a preservative.

EXAMPLE 6

A composition contains 15% by weight of substantially optically pure L-DFMO in a vehicle containing water 70.84%, glyceryl stearate 4.24%, polyethylene glycol 100-stearate 4.09%, cetearyl alcohol 3.05%, ceteareth-20 7.5%, urea 5%, mineral oil 2.22%, stearyl alcohol 1.67%, dimethicone 0.56%, and a preservative.

The composition should be topically applied to a selected area of the body from which it is desired to reduce hair growth. For example, the composition can be applied to the face, particularly to the beard area of the face, i.e., the cheek, neck, upper lip, or chin. The composition also may be used as an adjunct to other methods of hair removal including shaving, waxing, mechanical epilation, chemical depilation, electrolysis and laser-assisted hair removal.

The composition can also be applied to the legs, arms, torso or armpits. The composition is particularly suitable for reducing the growth of unwanted hair in women, particularly unwanted facial hair, for example, on the upper lip. The composition should be applied once or twice a day, or even more frequently, to achieve a perceived reduction in hair growth. Perception of reduced hair growth can occur as early as 24 hours or 48 hours (for instance, between normal shaving intervals) following use or can take up to, for example, three months. Reduction in hair growth is demonstrated when, for example, the rate of hair growth is slowed, the need for removal is reduced, the subject perceives less hair on the treated site, or quantitatively, when the weight of hair removed (i.e., hair mass) is reduced (quantitatively), subjects perceive a reduction, for example, in facial hair, or subjects are less concerned or bothered about their unwanted hair (e.g., facial hair).

Golden Syrian Hamster Assay

Male intact Golden Syrian hamsters are considered acceptable models for human beard hair growth in that they display oval shaped flank organs, one on each side, each about 8 mm. in major diameter. These organs produce fine light colored hair typical of the animal pelage found on the body. In response to androgens the flank organs produce dark coarse hair similar to male human beard hair. To evaluate the effectiveness of a composition, the flank organs of each of a group of hamsters are depilated by applying a thioglycolate-based chemical depilatory (Surgex) and/or shaved. To one organ of each animal 10 $\mu$l of vehicle alone once a day is applied, while to the other organ of each animal an equal amount of vehicle containing substantially optically pure L-DFMO, substantially optically pure D-DFMO, racemic DFMO, or non-racemic DFMO including a preponderance of L-DFMO. After thirteen applications (one application per day for five days a week), the flank organs are shaved and the amount of recovered hair (hair mass) from each is weighed. For certain experiments, where indicated, the treatment period was for less than 13 applications. The reduced treatment period allowed for determination of onset in activity. Percent-reduction of hair growth is calculated by subtracting the hair mass (mg) value of the test compound treated side from the hair mass value of the vehicle treated side; the delta value obtained is then divided by the hair mass value of the vehicle treated side, and the resultant number is multiplied by 100. Visual evaluations comparing hair regrowth between the drug treated and the vehicle control site were made generally on day-8, day-15 and on day-19. These observations provide an identification of onset in activity (and thus efficacy).

The above-described assay will be referred to herein as the "Golden Syrian Hamster" assay The efficacy of DFMO-containing compositions containing greater than 90% L-DFMO ("L-DFMO" for purposes of the below assays), racemic DFMO ("D,L-DFMO"), and greater than 90% D-DFMO (or "D-DFMO" for purposes of the below assays) was determined using the Golden Syrian Hamster assay. The L-DFMO produced a substantially greater hair mass reduction than the D-DFMO or D,L-DFMO (Table 1). The average inhibition at the 0.3% dose for the L-, D- and D,L-DFMO was 43±6%, 19±11% and 25±9%, respectively.

TABLE 1

| Treatment* | Dose | Hair Mass in mg (drug treated) | Hair mass in mg (vehicle treated) | Percent inhibition |
|---|---|---|---|---|
| D,L-DFMO | 0.3% | 1.53 ± 0.19 | 2.03 ± 0.15 | 25 ± 9 |
| D-DFMO | 0.3% | 1.39 ± 0.12 | 1.85 ± 0.24 | 19 ± 11 |
| L-DFMO | 0.3% | 1.06 ± 0.14 | 1.90 ± 0.20 | 43 ± 6 |
| Control | — | 2.60 ± 0.29 | 2.78 ± 0.28 | 3 ± 10 |

*The vehicle is described in Example 2.

The results of an assay of the visual efficacy of similar compositions tested at 2% concentration are presented in Table 2. The assay in a 'blinded' study included visual observations comparing the regrowth of hair on the DFMO treated flank organ with the vehicle treated flank organ during the course of treatment. Scores were assigned from 0 to +3. 0, no difference; +1, DFMO treated shorter than vehicle treated indicating efficacy; +2, DFMO treated much shorter than vehicle treated; +3, DFMO treated nearly bald indicating maximal efficacy. The results of the visual observations show a significant increase in the number of animals demonstrating efficacy with the L-DFMO treatment. Eighty-eight percent of the animals treated with L-DFMO vs. only 38% of the animals treated with D, L-DFMO showed efficacy following two weeks of applications (see Table 2). This data shows that an earlier onset in efficacy is achieved using the L-DFMO treatment. This assay will be referred to herein as the "Golden Syrian Hamster visual efficacy" assay.

TABLE 2

| Treatment* | Dose | Number of animals demonstrating efficacy (score of +1 or greater) after two weeks of treatment | Percent |
|---|---|---|---|
| D-DFMO | 2% | 2 out of 8 | 25% |
| L-DFMO | 2% | 7 out of 8 | 88% |
| D,L-DFMO | 2% | 3 out of 8 | 38% |

*The vehicle is described in Example 2.

In addition, there were unexpectedly large differences in DFMO enantiomer groups with regard to the number of animals demonstrating maximal efficacy. Sixty-three percent of the animals in the L-DFMO treatment group showed a maximal response, score of +3, as compared to only 13% in the racemic DFMO group and none in the D-DFMO group (see Table 3).

The visual observations on the percentage of animals attaining maximal efficacy serve as an excellent surrogate response for clinical observations on maximal responses in terms of marked reduction in visibility of facial hairs in humans.

TABLE 3

| Treatment* | Dose | Number of animals demonstrating maximal efficacy (observation score of +3) after full three weeks of treatment | Percent |
|---|---|---|---|
| D-DFMO | 2% | 0 out of 8 | 0% |
| L-DFMO | 2% | 5 out of 8 | 63% |
| D,L-DFMO | 2% | 1 out of 8 | 13% |

*The vehicle is described in Example 2.

Twice a Week Golden Syrian Hamster Assay

The Golden Syrian Hamster assay was modified so that the animals received a reduced treatment frequency with DFMO, namely twice per week instead of five times a week.

The results of this study show (see Table 4) that under this regimen, only the L-DFMO group demonstrated efficacy in reducing hair mass (about 30%). The D,L-DFMO and D-DFMO compositions were essentially inactive at the concentration used in the assay. This test demonstrates that compositions containing a preponderance of L-DFMO are efficacious at a reduced frequency of treatment compared to compositions containing D,L- or D-DFMO.

TABLE 4

| Treatment* | Dose 2×/wk | Hair Mass in mg (drug treated) | Hair mass in mg (vehicle treated) | Percent inhibition |
|---|---|---|---|---|
| D,L-DFMO | 1% | 1.74 ± 0.18 | 1.69 ± 0.13 | −4 ± 10 |
| D-DFMO | 1% | 1.80 ± 0.18 | 2.08 ± 0.15 | 8 ± 12 |
| L-DFMO | 1% | 1.83 ± 0.38 | 2.54 ± 0.31 | 29 ± 8 |
| Control | — | 2.60 ± 0.29 | 2.78 ± 0.28 | 3 ± 10 |

*The vehicle is Example 2.

Golden Syrian Hamster Hair Follicle Spatial Mass and Hair Follicle Density Assays Hamster flank organs were treated topically with D,L-DFMO or L-DFMO with the contra-lateral side treated with the carrier vehicle without DFMO. Animals were sacrificed at the indicated time-point (4 days or 7 days) and back skins containing the flank organ were removed for analysis. Glycerin was applied to the underside of the dorsal skin of the hamster flank organ regions. Flank organ hair follicle mass and density were assessed, by imaging the region with a digital camera, and analysis of the images was performed with Ultimage/Pro (version 2.5) software by Graftek. This technique permitted the quantification of hair follicle mass based on particle area and number, and hair follicle density based on particle number.

Table 5 shows that treatment with a 1% dose of DFMO for 4 days yields a hair follicle mass reduction that is 2-fold greater by L-DFMO enantiomer (43% inhibition) when compared to the decrease caused by D,L-DFMO (20% inhibition). When a lower 0.5% dose was applied for 7 days, the hair follicle mass reduction was nearly 4-fold greater by the L-DFMO treatment (58% inhibition) as compared to the D,L-DFMO (15% inhibition).

TABLE 5

| Treatment* | Treatment Period days | Dose % | Hair follicle mass as determined by image analysis: particle area (×10$^6$) Treated | Vehicle | Inhibition % |
|---|---|---|---|---|---|
| L-DFMO | 4 Days | 1 | 4.23 ± 1.1 | 7.24 ± 1.5 | 43 ± 9 |
| D,L-DFMO | 4 Days | 1 | 4.89 ± 0.9 | 5.96 ± 0.9 | 20 ± 9 |
| L-DFMO | 7 Days | 0.5 | 2.22 ± .94 | 3.89 ± 1.1 | 58 ± 11 |
| D,L-DFMO | 7 Days | 0.5 | 2.71 ± .71 | 3.40 ± .82 | 15 ± 13 |

*The vehicle is described in Example 2.

In another assay (Table 6), a similar 4-fold increase in efficacy was observed with the L-DFMO treatment. An L-DFMO dose of 0.5% applied topically for 7 days produced a 41% inhibition of hair follicle spatial mass over the vehicle treated control, whereas the D,L-DFMO produced a mere 9% reduction over the vehicle treated control group. When assessing hair follicle density, which indicates the number of follicles detected per unit area independent of their size, the L-DFMO enantiomer produced a 45% reduction, whereas D,L-DFMO had no effect on this efficacy parameter.

TABLE 6

| Treatment* | Treatment Period days | Dose % | % Inhibition of Hair Follicle Density | % Inhibition of Hair Follicle Mass |
|---|---|---|---|---|
| L-DFMO | 7 | 0.5 | 45 ± 5 | 41 ± 15 |
| D,L-DFMO | 7 | 0.5 | No Inhibition | 9 ± 20 |

*The vehicle is described in Example 2.

Overall, the results show a significant effect of L-DFMO in causing follicle shrinkage and hair follicle bulb density reduction at the low dose levels when compared to D,L-DFMO, which had either no effect (follicle density) or minimal effect (follicle spatial mass). These data indicate that compositions containing a preponderance of L-DFMO achieve a significantly earlier onset of activity and larger manifestation of effect than compositions including a similar concentration of D,L-DFMO.

Human Hair Follicle Growth Assay

Hair follicles were isolated from human facial (obtained from patients who underwent face lift surgery) skin samples using fine forceps under a dissecting microscope and grown in tissue culture Williams E medium—supplemented with insulin (10 µg/ml), glutamine (2 mM), hydrocortisone (100 µg/ml) and antibiotics/antimycotics (pen/strep). Hair lengths were determined on day 0, and day 7.

Human hair follicles in culture were treated with 0.5 mM concentration of L-DFMO, D-DFMO, D,L-DFMO. Controls were cultured in Williams E tissue culture medium without DFMO. The increase in hair fiber length was determined over seven days. The results of these analyses show that the hair follicle growth inhibitions (as compared to controls) were 1±12, 4±13, and 36±12% for the D,L-, D-, and L-DFMO, respectively. Only L-DFMO produced statistically significant reduction in hair growth (p=0.003) in this time period. This indicates that the percentage of subjects that respond to treatment with L-DFMO will be significantly higher than the percentage of subjects that respond to treatment with D,L-DFMO at the same concentration. The "P" values, as determined by paired test analysis, were 0.97, 0.78 and 0.003 for the D,L-DFMO, D-DFMO and L-DFMO, respectively.

Other embodiments are within the scope of the following 47s.

What is claimed is:

1. A method of reducing human hair growth, comprising
   selecting an area of skin from which reduced hair growth is desired; and
   applying to said area of skin a dermatologically acceptable composition comprising α-difluoromethylornithine in an amount effective to reduce hair growth, wherein the α-difluoromethylornithine comprises at least about 90% by weight of L-α-difluoromethylornithine.

2. The method of claim 1, wherein the α-difluoromethylornithine comprises at least about 95% L-α-difluoromethylornithine.

3. The method of claim 1, wherein the α-difluoromethylornithine comprises substantially optically pure L-α-difluoromethylornithine.

4. The method of claim 1, wherein the α-difluoromethylornithine is optically pure L-α-difluoromethylornithine.

5. The method of claim 1, 2, 3, or 4, wherein the composition has about 0.1% to about 30% of the α-difluoromethylornithine by weight.

6. The method of claim 5, wherein the composition has about 1% to about 20% of the α-difluoromethylornithine by weight.

7. The method of claim 5, wherein the composition has about 5% to about 15% of the α-difluoromethylornithine by weight.

8. The method of claim 1, wherein the area of skin is on the face.

9. The method of claim 1, wherein the α-difluoromethylornithine has a sufficient ratio of L-α-difluoromethylornithine relative to D-α-difluoromethylornithine so that the composition provides an average inhibition of hair growth of at least 35% when tested at an α-difluoromethylornithine concentration of 0.3% in the Golden Syrian Hamster assay.

10. The method of claim 9, wherein the composition provides an average inhibition of hair growth of at least 40% when tested at an α-difluoromethylornithine concentration of 0.3% in the Golden Syrian Hamster assay.

11. The method of claim 1, wherein the α-difluoromethylornithine has a sufficient ratio of L-α-difluoromethylornithine relative to D-α-diflouromethylornithine so that the composition exhibits efficacy in at least 60% of Golden Syrian Hamsters when tested at an α-difluoromethylornithine concentration of 2% in the Golden Syrian Hamster assay.

12. The method of claim 11, wherein the composition exhibits efficacy in at least 75% of Golden Syrian Hamsters when tested at an α-difluoromethylornithine concentration of 2% in the Golden Syrian Hamster assay.

13. The method of claim 1, wherein the α-difluoromethylornithine has a sufficient ratio of L-α-difluoromethylornithine relative to D-α-diflouromethylornithine so that the composition exhibits maximal efficacy in at least 40% of Golden Syrian Hamsters when tested at an L-α-difluoromethylornithine concentration of 2% in the Golden Syrian Hamster assay.

14. The method of claim 13, wherein the composition provides maximal efficacy in at least 50% of Golden Syrian Hamsters when tested at an α-difluoromethylornithine concentration of 2% in the Golden Syrian Hamster assay.

15. The method of claim 1, wherein the α-difluoromethylornithine has a sufficient ratio of L-α-difluoromethylornithine relative to D-α-diflouromethylornithine so that the composition provides an average inhibition of hair growth of at least 15% when tested at an α-difluoromethylornithine concentration of 1% in the twice a week Golden Syrian Hamster assay.

16. The method of claim 15, wherein the composition provides an average inhibition of hair growth of at least 20% when tested at an α-difluoromethylornithine concentration of 1% in the twice a week Golden Syrian Hamster assay.

17. The method of claim 1, wherein the α-difluoromethylornithine has a sufficient rati ratio of L-α-difluoromethylornithine relative to D-α-diflouromethylornithine so that the composition provides an average reduction of hair follicle spatial mass of at least 35% when tested at an α-difluoromethylornithine concentration of 0.5% in the Golden Syrian Hamster hair follicle mass assay.

18. The method of claim 17, wherein the composition provides an average reduction of hair follicle mass of at least 45% when tested at an α-difluoromethylornithine concentration of 0.5% in the Golden Syrian Hamster hair follicle mass assay.

19. The method of claim 1, wherein the α-difluoromethylornithine has a sufficient amount of L-α-difluoromethylornithine relative to D-α-diflouromethylornithine so the composition provides an average reduction of hair follicle density of at least 20% when tested at an α-difluoromethylornithine concentration of 0.5% in the Golden Syrian Hamster hair follicle density assay.

20. The method of claim 19, wherein the composition provides an average reduction of hair follicle density of at least 30% when tested at an α-difluoromethylornithine concentration of 0.5% in the Golden Syrian Hamster hair follicle density assay.

21. The method of claim 1, wherein the α-difluoromethylornithine has a sufficient ratio of L-α-difluoromethylornithine relative to D-α-diflouromethylornithine so that the α-difluoromethylornithine, when tested in the Human Hair Follicle Growth assay at a concentration of 0.5 mM, provides a hair follicle growth inhibition of at least 15%.

22. The method of claim 21, wherein the α-difluoromethylornithine provides a hair follicle growth inhibition of at least 25%.

23. The method of claim 1, wherein the composition produces less stinging, when applied to the face of a woman than a composition consisting of 15% by weight racemic α-diflouromethylornithine monohydrochloride monohydrate and 85% of a cream base consisting of

| Ingredient | Wt. Percent |
| --- | --- |
| Water | 80.84 |
| Glyceryl Stearate | 4.24 |
| PEG-100 Stearate | 4.09 |
| Cetearyl Alcohol | 3.05 |
| Ceteareth-20 | 2.50 |
| Mineral Oil | 2.22 |
| Stearyl Alcohol | 1.67 |
| Dimethicone | 0.56 |
| Citric Acid | — |
| Sodium Hydroxide | q.s. |

24. The method of claim 23, wherein the composition has about 5% to about 15% of the α-difluoromethylornithine by weight.

25. The method of claim 1, wherein the composition comprises from about 5% to about 15% by weight of the α-difluoromethylornithine and the α-difluoromethylornithine has sufficient L-α-difluoromethylornithine that the composition provides an earlier onset of facial hair growth reduction in women than a composition consisting of 15% by weight racemic α-diflouromehtylornithine monohydrochloride monohydrate and 85% of a cream base consisting of

| Ingredient | Wt. Percent |
| --- | --- |
| Water | 80.84 |
| Glyceryl Stearate | 4.24 |
| PEG-100 Stearate | 4.09 |
| Cetearyl Alcohol | 3.05 |
| Ceteareth-20 | 2.50 |
| Mineral Oil | 2.22 |
| Stearyl Alcohol | 1.67 |
| Dimethicone | 0.56 |
| Citric Acid | — |
| Sodium Hydroxide | q.s. |

26. The method of claim 1, wherein the composition comprises from about 5% to about 15% by weight of the α-difluoromethylornithine and the α-difluoromethylornithine has sufficient L-α-difluoromethylornithine that the composition provides a substantial reduction of facial hair in at least 50% of women when applied twice a day.

27. The method of claim 1, wherein the composition comprises from about 5% to about 15% by weight of the α-difluoromethylornithine and the α-difluoromethylornithine has sufficient L-α-difluoromethylornithine that the composition provides a substantially complete clearance of facial hair in at least 25% of women when applied twice a day.

28. The method of claim 1, wherein the composition comprises from about 1% to about 15% by weight of the α-difluoromethylornithine and the α-difluoromethylornithine has sufficient L-α-difluoromethylornithine so that the composition, when applied once a day to facial area in women, has at least the efficacy, when applied twice a day, of a composition consisting of 15% by weight racemic α-difluoromehtylornithine monohydrochloride monohydrate and 85% of a cream base consisting of

| Ingredient | Wt. Percent |
| --- | --- |
| Water | 80.84 |
| Glyceryl Stearate | 4.24 |
| PEG-100 Stearate | 4.09 |
| Cetearyl Alcohol | 3.05 |
| Ceteareth-20 | 2.50 |
| Mineral Oil | 2.22 |
| Stearyl Alcohol | 1.67 |
| Dimethicone | 0.56 |
| Citric Acid | — |
| Sodium Hydroxide | q.s. |

* * * * *

UNITED STATES PATENT AND TRADEMARK OFFICE
CERTIFICATE OF CORRECTION

PATENT NO.   : 6,743,822 B2
DATED        : June 1, 2004
INVENTOR(S)  : Peter Styczynski, Gurpreet S. Ahluwalia and Douglas Shander It is certified that error appears in the above-identified patent and that said Letters Patent is hereby corrected as shown below:

Column 10,
Line 61, before "ratio", delete "rati".

Column 11,
Line 9, insert -- that -- after "so".

Signed and Sealed this

Nineteenth Day of April, 2005

JON W. DUDAS
*Director of the United States Patent and Trademark Office*